United States Patent [19]

Leopardi et al.

[11] Patent Number: 5,514,339
[45] Date of Patent: May 7, 1996

[54] STOPPER OF ANALYSIS TEST TUBES

[76] Inventors: Francesco Leopardi, Via Palmanova, 24, 20132 Milano; Sergio Paoletti, Via Palatino, 3, 20148 Milano, both of Italy

[21] Appl. No.: 500,497

[22] Filed: Mar. 28, 1990

[30] Foreign Application Priority Data

Apr. 7, 1989 [IT] Italy .................................... 20067/89

[51] Int. Cl.⁶ ...................................................... B01L 3/14
[52] U.S. Cl. .......................... 422/99; 73/864.63; 215/247; 215/296; 215/298; 215/305; 220/229; 220/254; 220/256; 220/258; 220/306; 422/100; 422/102; 435/283.1; 604/3; 604/415
[58] Field of Search ............................. 422/99, 100, 102; 73/864.63, 864.86; 604/3, 415; 435/294, 295, 296, 299; 220/229, 254, 256, 258, 306; 215/247, 296, 298, 305

[56] References Cited

U.S. PATENT DOCUMENTS

| 4,197,735 | 4/1980 | Munzer et al. ............... 422/100 X |
| 4,409,988 | 10/1983 | Greenspan ..................... 435/294 |
| 4,539,855 | 9/1985 | Jacobs ........................... 73/864.25 |
| 4,786,471 | 11/1988 | Jones et al. .................... 422/102 |
| 4,789,639 | 12/1988 | Fleming ......................... 436/178 |
| 4,808,381 | 2/1989 | McGregor et al. ............ 422/100 |

Primary Examiner—Jill Warden
Assistant Examiner—Jan M. Ludlow
Attorney, Agent, or Firm—Nixon & Vanderhye

[57] ABSTRACT

A test tube stopper (1) has the shape of a small bowl and is provided with a protruding upper circular collar (11). The stopper (1) slidably enters into and seals the neck of a test tube (3) until the collar (11) rests against the mouth of the test tube (3). A horizontal bottom wall (12) of the stopper (1) is comprised of two or more elastically yielding sectors (16) which can bend under the action of a device (43) being introduced into the test tube (3) through the bottom wall (12) for introducing or withdrawing liquid. The resilient sectors (16) return to their initial position as soon as the device (43) has been extracted from the test tube (3) through the bottom wall (12). In a preferred embodiment a stopper (2), preferably of the conventional type, sealingly closes a cavity (14) of the stopper (1) to ensure sealing a vacuum previously provided in the test tube (3). The stopper (2) may then be removed when it is necessary to withdraw blood from the test tube (3).

8 Claims, 1 Drawing Sheet

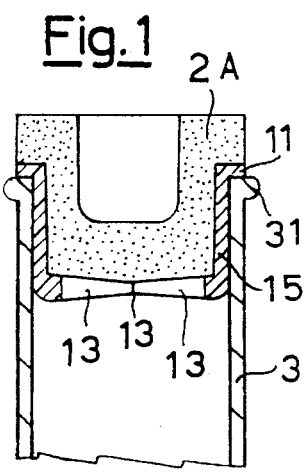
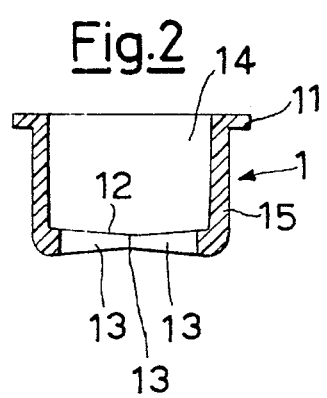
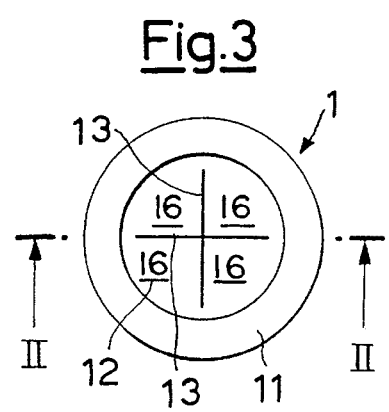
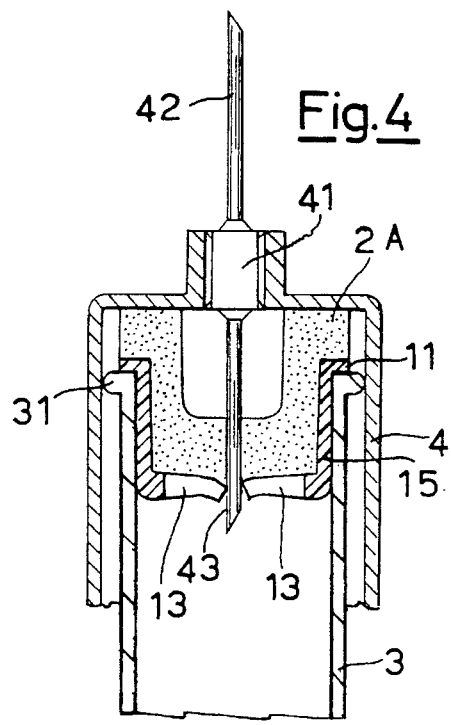
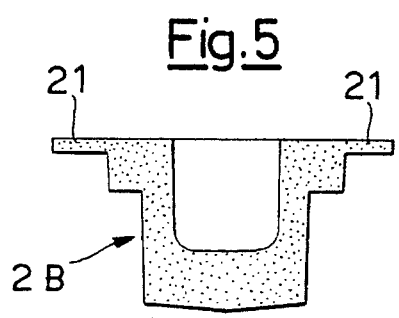
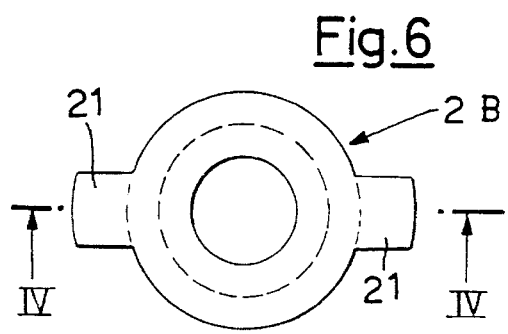
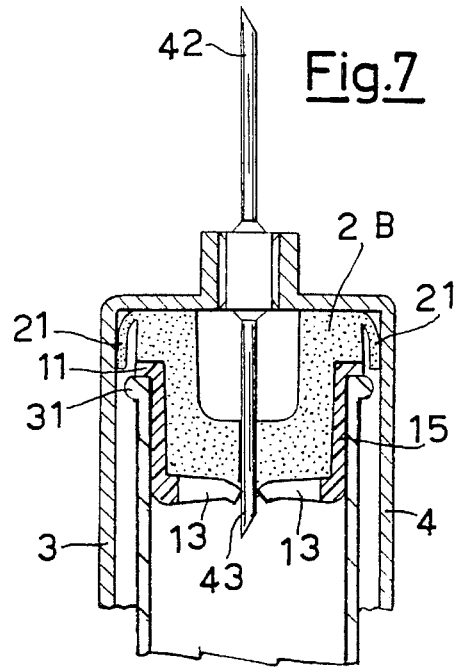

STOPPER OF ANALYSIS TEST TUBES

BACKGROUND

1. Field of the Invention

The present invention relates to a stopper for sealing analysis test tubes, which offers greater guarantees for the operator not to come into contact with the contents of the test tube, especially with blood.

2. Prior Art and Other Considerations

It is known that anybody who operates nowadays in the field of clinical and medical analyses must carefully avoid all contact with the blood to be analysed so as to avert any possible infection.

According to a first widely used technique, blood is taken from a patient by means of a disposable syringe and is then inserted into a test tube provided with a pierceable stopper. The test tube, containing the desired quantity of blood, may be sent to the analysis laboratory as it is, already stoppered but this presents some drawbacks which will be indicated later.

It is also known that for the taking of blood, instead of disposable syringes, the use is becoming increasingly widespread of test tubes inside which a predetermined vacuum has been created to withdraw the required quantity of blood, generally 2.5, 5 or 10 ml. Said test tubes are of glass and are closed by means of a sealing rubber stopper.

When blood is taken from the patient, the use is provided for a device known as a holder, generally made of rigid and transparent plastic material, of a substantially cylindrical shape, having one extremity open and communicating with the outside while the other extremity is closed by a bottom wall provided with an axial seat, generally threaded, for a twin-pointed disposable needle. The point of the needle facing the outside is introduced into the patient's vein while the point of the needle housed in the above holder is, by perforating the rubber stopper, introduced into the test tube under vacuum. The desired quantity of blood is thus recalled into the test tube.

Once the operation is over, the twin-pointed needle is removed from the seat provided and thrown away; the above holder may be used for another withdrawal and the test tube containing the desired quantity of blood may be sent to the laboratory as it is, already stoppered.

Whether the blood has been introduced into the test tube with the first or with the second technique, as often as not the stopper must be removed in the laboratory to withdraw from the test tube the blood to be analysed and during this stage, due to any drops of blood deposited on the lower part of the stopper, the operator runs the risk of coming into contact with blood during said removal.

The need is therefore still keenly felt for a stopper which can adequately protect the operator from accidental contact with blood from patients not only during the stage where blood is taken and handled but also during the stage where it is withdrawn from the test tube to carry out the analysis.

SUMMARY

The present invention proposes to solve the above problem by means of a stopper, which has the shape of a small bowl and is provided with a protruding upper circular collar and with a substantially horizontal bottom wall, said stopper slidably entering into and sealing the neck of said test tube until said collar rests on the rim of the mouth of said test tube, characterized in that said horizontal bottom wall is constituted by two or more elastically yielding sectors which can bend, under the action of a device inserted into said test tube through said wall to introduce or withdraw a liquid, and which then return to their initial position as soon as said device has been extracted from said test tube through said wall.

In a preferred embodiment, the cavity of the stopper according to the present invention is sealingly closed by means of a pierceable stopper of the traditional type to ensure sealing the vacuum previously provided in the test tube and only the stopper of the traditional type is removed when it is necessary to withdraw the liquid, in particular blood, from the test tube or to introduce the liquid into the test tube.

Both the stoppers are preferably made of rubber, or of plastic rubber, or of other elastic thermoplastic polymers.

The number of elastically yielding sectors making up the substantially horizontal bottom wall of the stopper according to the present invention ranges preferably from 2 to 10; even more preferably the above sectors are 4.

As shall appear even more evident from the description which follows, the stopper according to the present invention protects the operator from accidental contact with the liquid, particularly blood, contained in the test tube while still, thanks to the above elastically yielding sectors, allowing the withdrawal of the liquid contained in the test tube when this becomes necessary for carrying out analyses and tests. In addition, the above elastically yielding sectors scrape against the withdrawal device, such as, say, a pipette, when the latter, having been immersed into the test tube, is withdrawn from it. Any drops of liquid, in particular blood, which have been deposited on the walls of said device during the withdrawal operation are thus removed. There is therefore accomplished a high degree of cleaning of the withdrawal device, which is not, on the other hand, possible in the case of test tube sealing devices of the traditional type.

It is thus important that the edges of the elastically yielding sectors which constitute the substantially horizontal bottom wall of the stopper according to the present invention be in close contact with one another so that, during the at rest position at atmospheric pressure, they ensure a sufficient sealing of the liquid contained in the test tube.

This can be obtained by the use of known materials and techniques; for example, by obtaining the above elastically yielding sectors by means of a punch cutter provided with very sharp blades which do not remove any quantity of material and by making the wall from which said mobile sectors are obtained sufficiently thick.

BRIEF DESCRIPTION OF THE DRAWINGS

The present invention is illustrated, as a non-limiting example, in the enclosed table of drawings, wherein:

FIG. 1 is a vertical cross-sectional view of a test tube, partially illustrated, on which there is mounted a stopper according to the present invention. In addition, the cavity of said stopper is sealingly closed by a pierceable stopper of the traditional type;

FIG. 2 is a vertical cross-sectional view taken along the line II—II of FIG. 3 of the stopper according to the present invention;

FIG. 3 is a plan view from above of the stopper illustrated in the preceding FIG. 2;

FIG. 4 is a vertical cross-sectional view of a holder, represented in part, coupled with the test tube of FIG. 1;

FIG. 5 is a vertical cross-sectional view, taken along the line IV—IV of FIG. 6, of a pierceable stopper of the traditional type suitable for ensuring the sealed closing of the stopper according to the present invention when this is used to seal a test tube in which some vacuum has been previously provided;

FIG. 6 is a plan view from above of the pierceable stopper of the traditional type illustrated in the preceding FIG. 5;

FIG. 7 corresponds to the preceding FIG. 4 except that the stopper is that of FIGS. 5 and 6.

DETAILED DESCRIPTION OF THE DRAWINGS

As can be seen from FIGS. 1 to 7, the stopper (1) has the shape of a small bowl and is provided with a protruding circular collar (11).

The stopper (1) slidably enters into and seals the neck of a test tube (3) until the collar (11) rests against the rim (31) of the mouth of the test tube (3).

The lower portion of said stopper (1) is provided with a bottom wall (12), substantially horizontal, constituted by 4 elastically yielding sectors (16) capable of bending elastically (FIGS. 4 and 7) under the action of a device (43) inserted into said test tube (3), through said bottom wall (12), to introduce into (or withdraw from) it a liquid, in particular blood, and which then return to their initial position (FIG. 1) as soon as the device (43) has been extracted from the test tube (3) through said bottom wall (12).

The stopper (1) is preferably made of rubber, or of plastic rubber, or of other elastic thermoplastic polymers.

The number of elastically yielding sectors (16) comprising the substantially horizontal bottom wall (12) of the stopper (1) preferably ranges from 2 to 10. As illustrated in FIG. 3, the preferred number of sectors (16) is four.

The sectors (16) are obtained by punching or cutting the bottom wall (12), as by using a punch cutter provided with very sharp blades so as not to remove any quantity of material from the bottom wall (12) or otherwise reduce the thickness of the sectors (16). The sectors (16) thus have edges (13) formed by the punching or cutting operation. The sector edges (13) are in close contact with one another.

The bottom wall (12) is thus spaced away from the upper circular collar (11) to define a cavity (14) for receiving a pierceable member.

In the case of test tubes under vacuum a pierceable stopper of the traditional type (2A or 2B) sealingly closes the cavity (14) of the stopper (1) to ensure sealing the vacuum provided in the test tube (3). For greater safety the external vertical well (15) of the stopper (1) may be glued to the inside of the neck (FIG. 1) of the test tube (3) which may be either of glass or of a thermoplastic polymer. The vertical wall is essentially cylindrical in shape.

The test tube thus sealed (FIG. 1) maintains the predetermined vacuum, which has been provided therein, until the moment when it is necessary to take the patient's blood. At this point use is made of a known type of holder, already described previously and illustrated in FIGS. 4 and 7. The external element (42) of a twin-pointed disposable needle introduced into the patient's vein. Then the internal element (43) of the needle is introduced into the test tube (3) by perforating the pierceable stopper of the traditional type (2A or 2B) and by bending the elastically yielding sectors (16) of the first stopper (1). A predetermined quantity of blood thus flows from the patient's vein to the test tube (3). The holder is then slipped off and the test tube is delivered to the analyst. The analyst removes the pierceable stopper of the traditional type (2A or 2B). The pierceable stopper of the traditional type illustrated in FIGS. 1 and 4, differs from that of FIG. 5 to 7 because the latter is provided with two flaps (21) which have the exact purpose of facilitating the removal of said pierceable stopper of the traditional type on the part of the analyst.

The provision of the resilient sectors (16) of the stopper (1) of the present invention protects the operator from accidental contact with the liquid, particularly blood, contained in the test tube (3), while allowing the withdrawal of the liquid contained in the test tube (3) when this becomes necessary for conducting analyses and tests. In addition, the elastically yielding sectors (16) scrape against the withdrawal device (43), such as a pipette for example, when the withdrawal device has been immersed into the test tube (3) and is being withdrawn therefrom. Any drops of liquid, such as blood, which have been deposited on the walls of the device (43) during the withdrawal operation, are thus removed. Advantageously, the sectors (16) provide a cleaning of the withdrawal device (43), which is not realized by test tube sealing devices of the traditional type.

After removing the pierceable stopper of the traditional type (2A or 2B) the blood contained in test tube (3) is still separated from the outside by the stopper (1) according to the present invention. In spite of this the analyst may withdraw blood from tile test tube (3) by inserting a pipett through the bottom wall (12) of the stopper (1) according to the present invention as previously described.

We claim:

1. A stopper for sealing insertion into a mouth of a test tube, the stopper comprising:

a protruding upper circular collar for resting on a rim of the mouth of the test tube;

an essentially cylindrical vertical wall upon which the protruding upper circular collar is surmounted;

an essentially horizontal bottom wall connected to the vertical wall, the bottom wall being spaced away from the upper circular collar to define a cavity for receiving a pierceable member, the bottom wall comprising a plurality of elastically yielding sectors for closing the bottom of the cavity and thereby providing a bowl shape for the stopper when the plurality of sectors are in an initial position, the plurality of sectors being bendable when a device is inserted into the test tube through the bottom wall, the plurality of sectors further being resiliently returnable to the initial position when the device is extracted from the test tube through the bottom wall.

2. A stopper according to claim 1, wherein the number of elastically yielding sectors which comprise said bottom wall ranges from 2 to 10.

3. A stopper according to claim 2, wherein the number of elastically yielding sectors is 4.

4. A stopper according to claim 1, wherein said plurality of elastically yielding sectors have edges which are in close contact with one another.

5. A stopper for sealing insertion into a mouth of a test tube in combination with a pierceable member, the stopper comprising:

a protruding upper circular collar for resting on a rim of the mouth of the test tube;

an essentially cylindrical vertical wall upon which the protruding upper circular collar is surmounted;

an essentially horizontal bottom wall connected to the vertical wall, the bottom wall being spaced away from the upper circular collar to define a cavity for receiving the pierceable member, the bottom wall comprising a plurality of elastically yielding sectors for closing the bottom of the cavity and thereby providing a bowl shape for the stopper when the plurality of sectors are in an initial position, the plurality of sectors being bendable when a device is inserted into the test tube through the bottom wall, the plurality of sectors further being resiliently returnable to the initial position when the device is extracted from the test tube through the bottom wall.

6. A stopper according to claim 5, wherein the number of elastically yielding sectors which comprise said bottom wall ranges from 2 to 10.

7. A stopper according to claim 6, wherein the number of elastically yielding sectors is 4.

8. A stopper according to claim 5, wherein said plurality of elastically yielding sectors have edges which are in close contact with one another.

\* \* \* \* \*